United States Patent [19]

Sackett

[11] Patent Number: 5,787,896

[45] Date of Patent: Aug. 4, 1998

[54] METHOD AND APPARATUS FOR AN ULNAR COLLATERAL LIGAMENT THUMB SUPPORT

[76] Inventor: Tod Sackett, 124 Industrial Pkwy., Chardon, Ohio 44024

[21] Appl. No.: 770,055

[22] Filed: Dec. 19, 1996

[51] Int. Cl.⁶ .................................................. A61F 5/37
[52] U.S. Cl. .................................................. 128/880; 602/22
[58] Field of Search ............................ 128/846, 877, 128/878, 879, 880; 602/5, 21, 22; 2/162, 161.1, 161.2, 161.3, 161.4, 161.5, 161.6

[56] References Cited

U.S. PATENT DOCUMENTS

| | | | |
|---|---|---|---|
| 4,524,464 | 6/1985 | Primiano | 128/879 |
| 4,653,490 | 3/1987 | Eisenberg | 128/880 |
| 4,709,694 | 12/1987 | O'Connell . | |
| 4,787,376 | 11/1988 | Eisenberg | 128/880 |
| 4,862,877 | 9/1989 | Barber . | |
| 5,058,209 | 10/1991 | Eisenberg . | |
| 5,083,314 | 1/1992 | Anduhar . | |
| 5,121,943 | 6/1992 | Proctor . | |
| 5,152,739 | 10/1992 | Grob . | |
| 5,152,740 | 10/1992 | Harkensee et al. . | |
| 5,197,149 | 3/1993 | Overton | 2/161.4 |
| 5,295,948 | 3/1994 | Gray | 128/882 |
| 5,312,134 | 5/1994 | Goode et al. . | |

*Primary Examiner*—Michael A. Brown
*Attorney, Agent, or Firm*—Joseph H. Taddeo

[57] ABSTRACT

A specialized immobilizing splint that is adapted for protection of an injured thumb, where the person who sustained the injury may continue activities with the diminished risk of re-injury. A skier with an injury to the ulnar collateral ligament (UCL) may use this splint to immobilize the thumb without diminishing the strength of his grip. The glove is the basic element that retains the splinting device and maintains it in place. The plastic splint gives support to the thumb at the metacarpophalangeal articulation and the associated ulnar collateral ligament. The tensioning strap assists the thumb in its gripping motion because of the positioning of this strap in relation to its point of attachment. The thumb is also protected from hyperextension in the areas where it is supported.

24 Claims, 3 Drawing Sheets

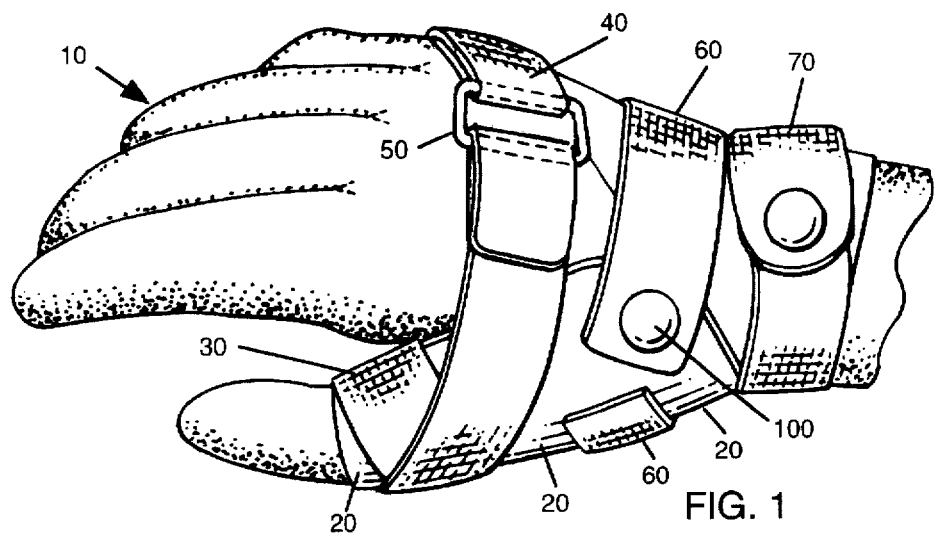
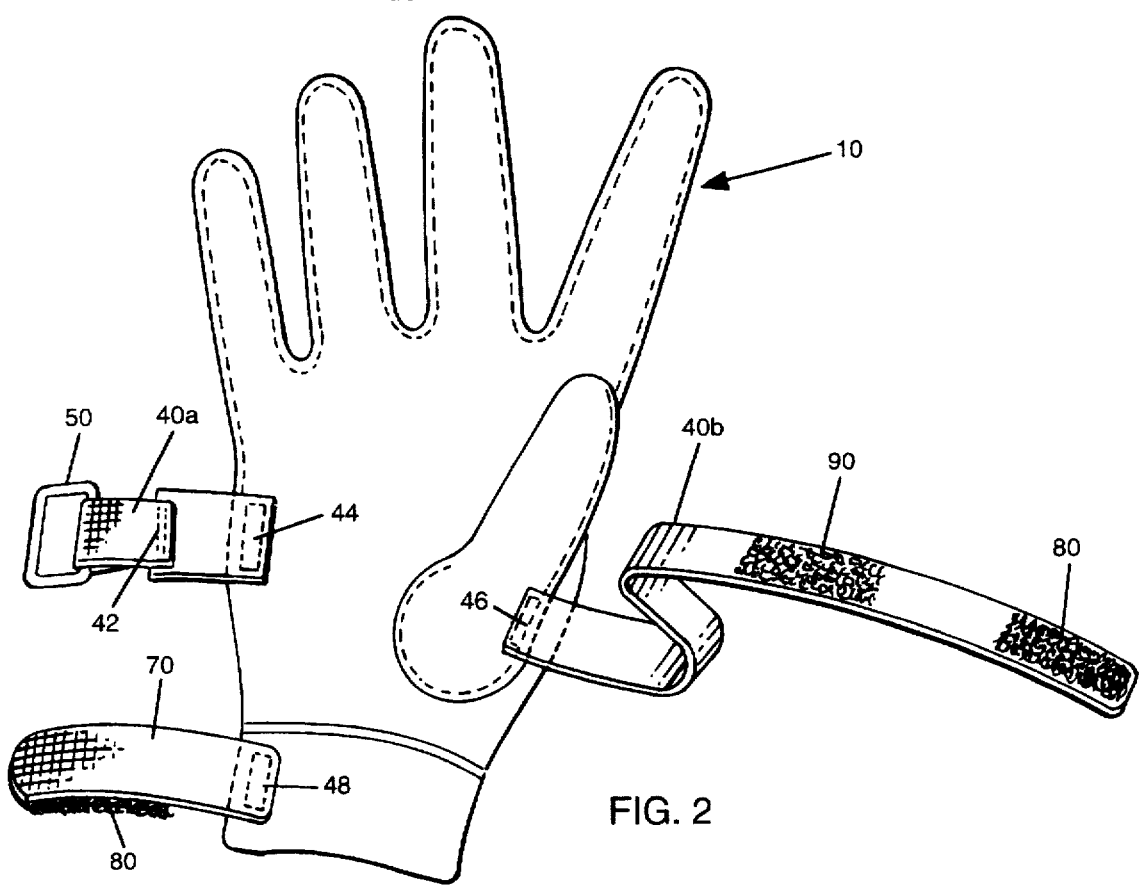

METHOD AND APPARATUS FOR AN ULNAR COLLATERAL LIGAMENT THUMB SUPPORT

REFERENCE TO PREVIOUSLY FILED APPLICATIONS

Your applicant makes reference to the disclosure document heretofore filed by him, as follows:

Disclosure Document No. 407292, submitted Oct. 22, 1996.

FIELD OF INVENTION

The present invention relates to a specialized immobilizing splint that is adapted for protection of an injured thumb, and more particularly to a splint whereby the person who sustained the injury may continue activities with the diminished risk of re-injury. A skier with an injury to the ulnar collateral ligament (UCL) may use this splint to immobilize the thumb without diminishing the strength of his grip.

BACKGROUND OF THE INVENTION

Skiers and other athletes commonly suffer from hyperextension of the thumb with consequent strain, stretching or tearing of the ulnar collateral ligament. This is so common that orthopedic surgeons, medical care providers and others have coined the term, "Skiers Thumb", for this condition. Under these circumstances, the standard medical advice is cease participation in the activity that caused the trauma, for the weakened thumb is more susceptible to injury. Also, in the case of skiers, this type injury substantially reduces the skier's ability to grasp and maintain a firm grip on the pole.

U.S. Pat. No. 5,152,740, granted Oct. 6, 1992, to P. M. Harkensee, et al, teaches of an inflatable hand splint that is formed of a bladder adapted to fit in the palm of a patient's hand between the thumb and fingers. The inflation and deflation of the bladder is controlled by the patient to fit his particular need.

U.S. Pat. No. 5,083,314, granted Jan. 28, 1992, to E. M. Andujar, discloses a sports glove for use in contact sports. It is comprised of a unitary molded body so that it protects the wrist, hand, fingers and thumb. A protective pad is secured to the back of the hand portion and is covered by a smooth plastic coating.

U.S. Pat. No. 5,058,209, granted Oct. 22, 1991, to J. H. Eisenberg, discloses a glove for protecting the ulnar collateral ligament. A thumb pocket of the glove is connected to the finger portion away from the rest of the glove, to prevent damage to the ligaments in the event the user's thumb be abnormally bent.

U.S. Pat. No. 4,862,877, granted Sep. 5, 1989, to L. M. Barber, discloses a hand splint that leaves the volar wrist free and which can be used by itself or as a foundation splint for the attachment of various permanent and removable, hand and finger corrective devices.

U.S. Pat. No. 4,709,694, granted Dec. 1, 1987, to B. O'Connell, discloses a dynamic splint for treating the hands of persons having spastic conditions. The glove-like covering is made of a stretch material which covers the palm and the back of the hand.

Several of the referenced prior art disclose protective sports gloves that protect the hands, fingers and thumbs, but do not immobilize the injured thumb. Another uses a dynamic splint to treat a spastic condition, where others are only designed to protect from contact abrasions or from the cold and not to protect from damaging the ligaments in one's thumb. Still others utilize the immobilization of the ulnar collateral ligament by inserting the thumb and second metacarpal finger in one pocket to irrigidly immobilize the use of the thumb to reduce the stress on that ligament.

Therefore, there is a particular need for a splint that is designed for use in medical applications, where the user has need of a functional support at the metacarpophalangeal (MP) articulation and the associated ulnar collateral ligament for continued participation in the sport in which the injury occurred.

SUMMARY OF THE INVENTION

The present invention is directed to a form-fitting sports-glove and a conformably designed rigid thumb splint.

Attached to the sports glove are several straps to control the fit and conformity of the glove; the first being a tensioning strap proceeding nearer from the base of thumb, proceeding around the ulnar side of the second phalange toward the palmar surface, exiting the plastic splint, encircling the thumb, traversing the back of the hand, through a tensioning loop to control the tension exerted on the splint; the second being a wrist strap, which encircles the wrist, while maintaining the positioning of the glove.

The conformable thumb splint, made from a sheet of rigid plastic or equivalent, has two straps attached to it; the first being a sizing strap that is placed around the second phalange of the thumb, the second, a positioning strap, encircling the wrist, and attaching to the opposite side of the splint, to secure the splint in place. In applying the repositioning thumb splint, it is thermally shaped and heat treated to conform to the desired shape to retain the positioning of the injured member.

In the preferred embodiment, hook and pile fasteners, more commonly referred to as Velcro™, are used to secure the glove and splint to provide the proper amount of tension.

It is therefore an object of the present invention to provide a specialized glove with a repositioning thumb splint that can be applied to a person sustaining an injury to his thumb to prevent further injury or damage, such as a rupture or tearing, to the ulnar collateral ligament.

It is another object of the present invention to provide a specialized glove with a repositioning thumb splint that can be applied to a person sustaining an injury to his thumb so that he may continue his activities with diminished risk of re-injury.

It is still another object of the present invention to provide a specialized glove with a repositioning thumb splint that immobilizes the thumb without diminishing the strength of the grip.

Yet, it is another object of the present invention to provide a specialized glove having a plurality of straps to provide the proper tension to control the location and positioning of the rigid thumb splint.

Still, it is another object of the present invention to provide a repositioning thumb splint having a plurality of straps to control the fit and function of the splint.

One additional object of the present invention to provide a specialized glove with repositioning thumb splint that can be worn comfortably by the user without creating undue fatigue or discomfort to the wearer.

It is a final object of the present invention to provide a repositioning thumb splint that is thermally shaped and heat treated to conform to the desired shape to retain the positioning of the injured member.

These and other advantages of the present invention will become more apparent upon further reading of the detailed specification. It should be understood that deviations or modifications can be made without deviating or departing from the spirit of the present invention.

BRIEF DESCRIPTION OF THE DRAWINGS

FIG. 1 depicts a perspective view of the right-handed glove with the formed thumb splint protecting and immobilizing the thumb.

FIG. 2 shows a typical palmar view of the glove of the preferred embodiment, designed for use on one's right hand.

DETAILED DESCRIPTION OF THE PREFERRED EMBODIMENT

Figure 3:
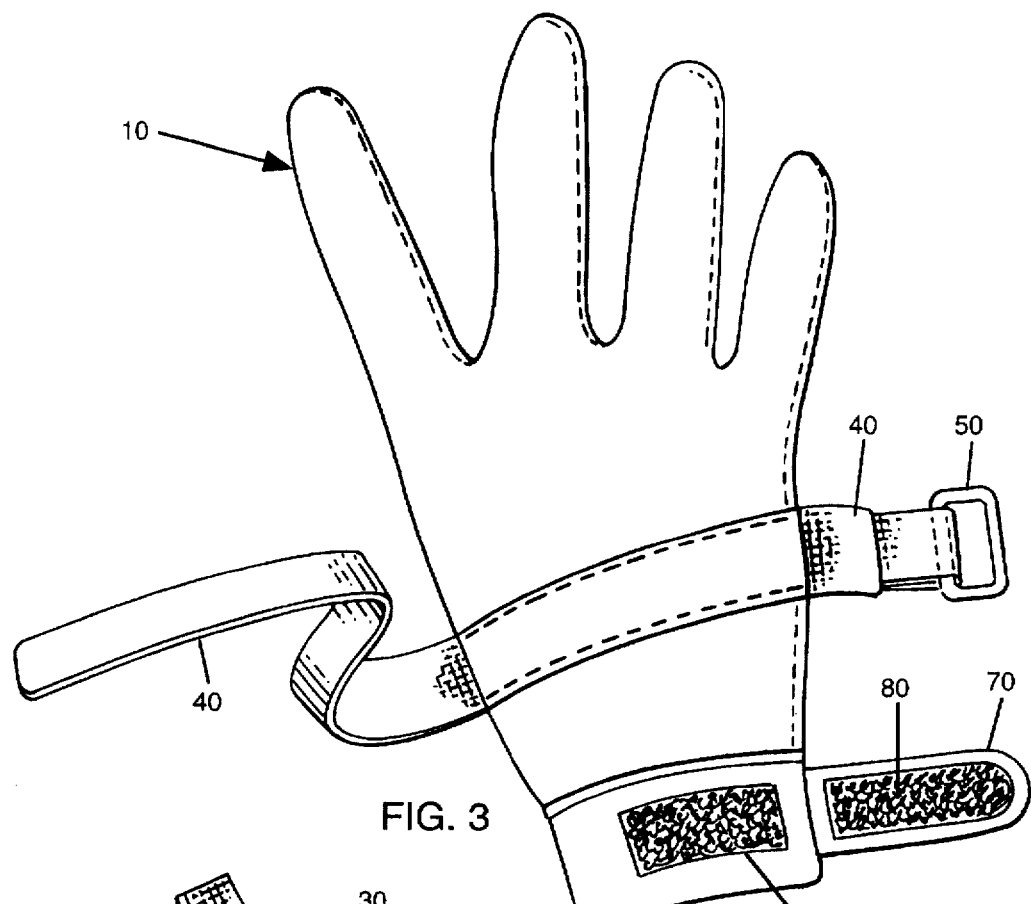
FIG. 3 depicts a typical back view of the right-handed glove of the preferred embodiment.

The present invention details a specialized immobilizing support or splint that is adapted for protection of an injured thumb. A person who sustained the injury may continue his activities by lessening the risk of re-injury. For example, a skier who injures his ulnar collateral ligament may use this splint to immobilize the thumb without lessening the strength of his grip.

As shown in FIG. 1, the present invention comprises a utility sports glove 10 and a repositioning splint 20. The splint sizing strap 30 holds the plastic splint 20 in place around the second phalange of the thumb. In the preferred embodiment, a hook and loop fastening system, such as Velcro, is used to retain the heat treated splint 20 in its pre-adjusted position. This strap 30 is subsequently wrapped around the splint 20 and ultimately upon itself.

The tensioning strap 40 is attached to the glove 10 along the first metacarpal of the thumb, nearer to the base of the thumb or thumb joint. The tensioning strap 40 proceeds around the ulnar side of the second phalange toward the palmar surface, exiting the plastic splint 20, and completing the circle around the thumb, where it traverses the back of the hand to a tensioning loop 50 to produce a mechanical advantage that controls a tension exerted on the plastic portion of the splint 20. The tensioning strap 40 proceeds through the splint 20 and exits the splint underneath the splint thumb tab 28, so as to effect greater control over thumb by tensioning the thumb inward and enhancing grip strength.

In use, the tensioning strap 40 that commences at an attachment point near the base of the thumb, is wrapped partially around an inner thumb surface, and further through and around the outside of the splint 20 for insertion through tensioning loop 50, folding and anchoring on itself when a comfortable tension is achieved. The strap 40 is then fastened at the desired tension and location with a hook 80 and loop 90 fastening system (FIG. 3), such as Velcro, using a pressure sensitive adhesive. The function of this strap 40 is to provide additional support to the thumb at the MP joint and its associated supporting ligaments. An important additional benefit of the tensioning strap 40 is that when the user grips an object, the geometry of the hand is such that the width of the palm area naturally expands. The positioning of the strap 40 on the back of the hand, coacting with the tensioning loop 50 that emanates from the outer palm area, is such that expansion of the hand by gripping, concomitantly pulls the thumb inward against the hand and toward the index finger, thereby increasing gripping power and protection for the thumb.

The positioning strap 60, which is attached to the splint 20 by strap retainer 100, circles the wrist and using hook and loop fasteners, attaches to the opposite side of the splint 20, thereby further securing the splint in place.

In an alternate embodiment, a coating of pressure sensitive adhesive is used on the inner surface of the strap 30 to secure it to the thermally formed splint 20.

FIG. 2 shows the palmar surface of the sports glove and the associated straps that are attached to it. The tension strap 40 is comprised of two assemblies; the first, a strap portion 40b of about 11 inches in length; the second, a mating strap 40a, of about one inch in length, having tension loop 50 at the unattached end. The tension strap 40a is sewn to the glove at the first metacarpal portion of the thumb cavity, which is near to the base of the thumb projection. At the opposite end are the attachment PSAs, or pressure sensitive adhesives, that are the hook fastener 80 and toward the mid-section, the loop or pile fastener 90. The mating strap 40a is sewn to the glove, near the vicinity of the base of the little finger, at location 44. The tension loop 50 is secured to the mating tension strap 40a by passing the loose end through the tension loop, folding it over, then stitching it in place.

Shown in FIG. 3 is the detailed assembly of the adjustable wrist strap 70. The loop or pile fastener 80 is secured, using a pressure sensitive adhesive, to the loose end of the adjustable wrist strap 70. It, in turn mates with the loop fastener 90 that is attached to the glove using a pressure sensitive adhesive.

Figure 4:
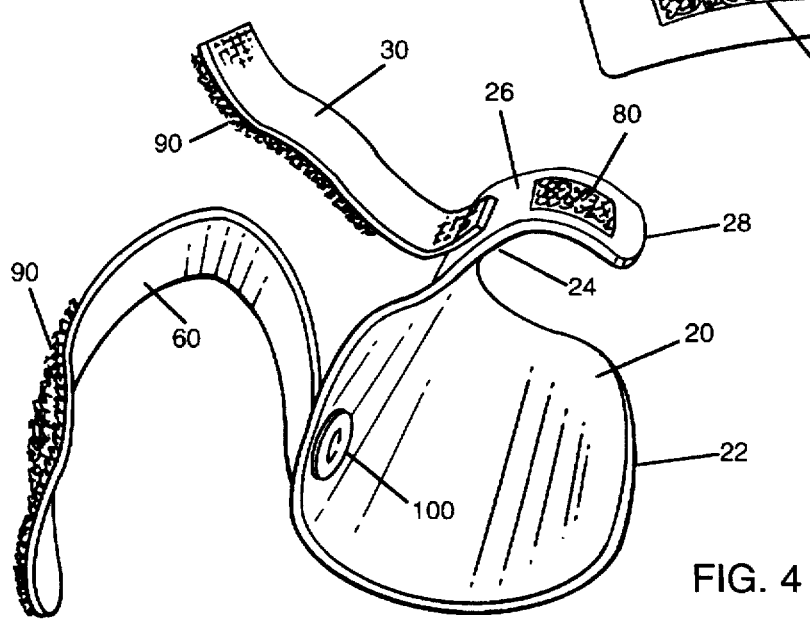
FIG. 4 is a perspective view of a typical thermally formed thumb splint.

Turning now to FIG. 4, depicted is a perspective view of the rigid immobilizing thumb splint 20. It is formed of a moldable material, for shaping the splint 20 for conformity to an individual thumb and thumb joint area of the hand by means of low temperature heat treatment. The protective attribute of the thumb splint 20 is preferably provided by the wider body portion 22, leading to a narrower, integral neck piece 24. The narrower neck provides a degree of flexibility to a smaller, integral headpiece 26 that culminates in a projecting thumb tab 28.

There are a plurality of straps, preferably two straps, that control the fit and function of the splint 20. The splint sizing strap 30 is designed to wrap around tab 28 and to hold the plastic splint 20 in place around the second phalange of the thumb. A loop or pile fastener 90 is attached beneath the free end of sizing strap 30. When the sizing strap encircles the end of the thumb, it then mates with the loop fastener 80 that is cemented to the splint 20.

Nearer to the base of the thumb is the positioning strap 60, which is attached to the wider body portion 22 of splint 20 by strap retainer 100. In application, it encircles around the wrist and attaches to the opposite side of the splint 20, thereby further securing the splint in place. A loop or pile fastener 90 is attached to the free end of the positioning strap 60, using a pressure sensitive adhesive, that will mate with a loop fastener 80 secured to the bottom portion of the splint with a pressure sensitive adhesive, as is best illustrated in FIG. 5.

Figure 5:
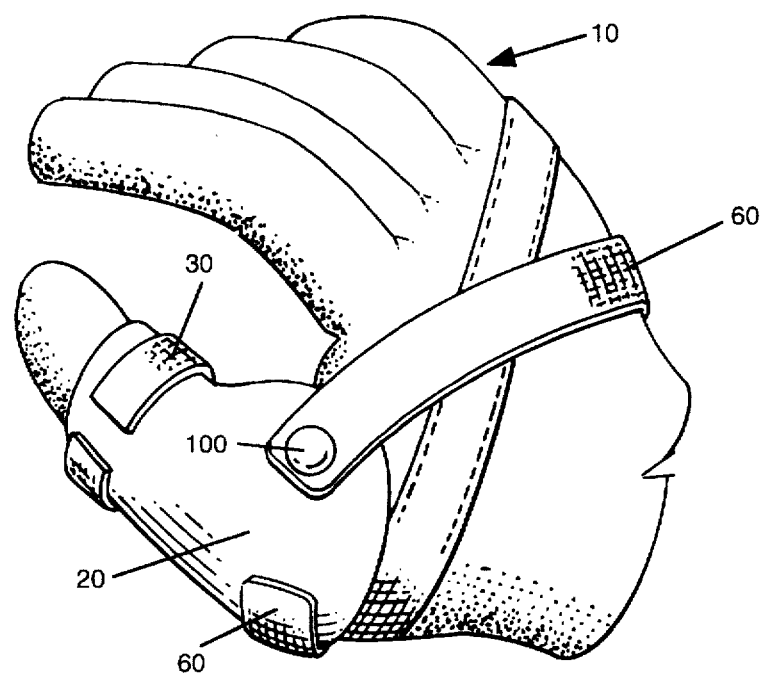
FIG. 5 depicts a perspective view of the right-handed glove with the formed thumb splint prior to introducing the protective tensioning straps.

FIG. 5 shows the splint 20 mounted over the glove 10 before the tension strap 40 is applied. The splint sizing strap 30 is shown in place holding the plastic splint 20 as it encircles the second phalange of the thumb. Also shown is the positioning strap 60 as it encircles the wrist and attaches to the opposite side of the splint 20.

Figure 6:
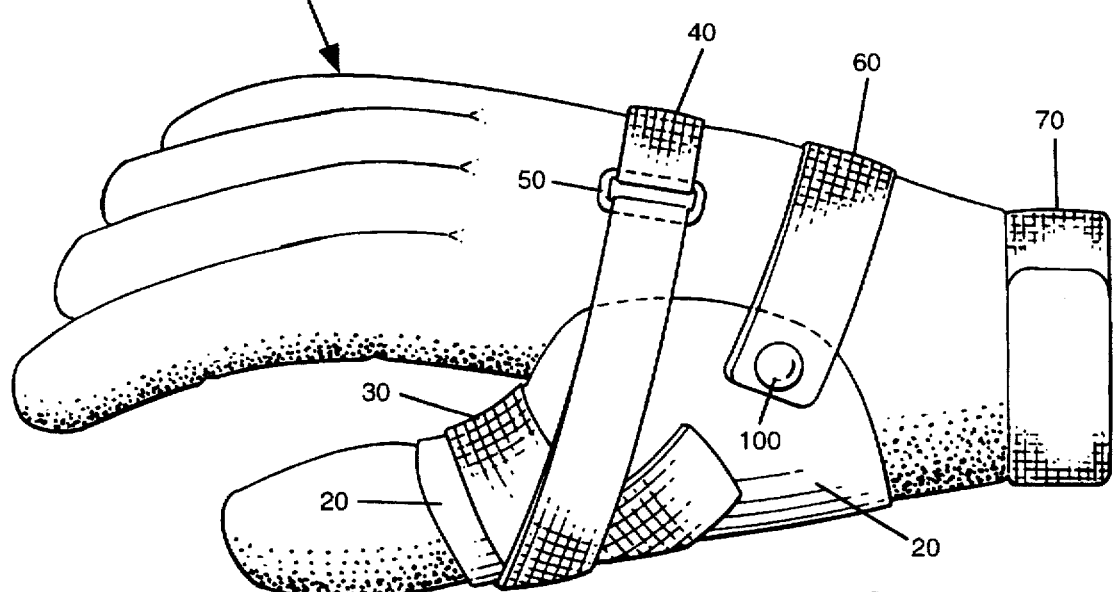
FIG. 6 is a detailed side elevation illustrating the use and positioning of the adjustable straps holding.

Referring to FIG. 6, the glove and splint assembly is shown in a side elevation, best illustrating the placement of the straps to complete the final strap positioning.

The following procedure can be used in implementing the application of this invention.

1. The hand with the injured thumb should be carefully inserted into the glove.
2. The wrist strap 70 should be closely fitted around the wrist.
3. Place the thumb splint 20 over the injured thumb.
4. Carefully wrap sizing strap 30 around the second phalange of the thumb, securing it with the hook and loop fastener.
5. Positioning strap 60 is then drawn around the back of the hand and subsequently attached to the opposite side, at the bottom of the splint.
6. The tensioning strap 40b is next placed between the thumb and forefinger, encircling the splinted thumb, passing through the tension loop 50, found at the end of strap 40a, folded back upon itself, and fastened with the hook and loop fasteners to the desired placement and tension.
7. This completes the installation.

While specific embodiments of the present invention have been shown and described in detail to illustrate the principles of the invention, it should be understood the that other modifications or embellishments can be made without departing from the true spirit of the invention.

I claim:

1. A thumb support for use by a person having an injured thumb for enabling continued participation in sporting activities with diminished risk of reinjury, but without diminishing grip strength, the thumb support comprising:

a glove that includes a glove strap system having associated straps attached to the glove;

means for stabilizing an injured thumb, said means including a narrowed integral flex portion fitted over the glove, wherein the means for stabilizing comprises a repositioning thumb splint mounted over the glove to immobilize and fortify an injured thumb while maintaining grip strength provided by a thumb; the splint including a splint strap system with a plurality of splint straps secured to the splint straps secured to the splint for retaining the splint in a preferred position on an injured thumb.

2. An immobilizing thumb support according to claim 1, wherein the thumb splint is constructed of a thermally moldable material, whereby the splint can be thermally shaped for conformity to an injured thumb.

3. An immobilizing thumb support according to claim 2, wherein the repositioning thumb splint is a preformed rigid piece fitted over the glove.

4. An immobilizing thumb support according to claim 3, wherein the plurality of splint straps in the splint strap system comprises a splint sizing strap having first and second ends with the first end fixed to the splint and the second end having a pressure sensitive adhesive to retain the splint in a pre-adjusted position and to secure the sizing strap second end that is wrapped around the splint.

5. An immobilizing thumb support according to claim 4, wherein the plurality of splint straps of the splint strap system further comprises a splint positioning strap having first and second ends, a strap retainer fixed to the splint for attachment of the positioning strap first end to the splint, the second positioning strap end having a pressure sensitive adhesive to secure the positioning strap second end that is wrapped around a person's wrist to the splint.

6. An immobilizing thumb support according to claim 5, the straps of the glove strap system comprising a tensioning strap having first and second ends and a mid-section, the tensioning strap first end fixed to the glove near a thumb base, the second tensioning strap end and mid-section having pressure sensitive adhesive;

a mating strap having first and second ends, the mating strap first end fixed to the glove near a base of a little finger and a tension loop secured to the second end of the mating strap to receive the tensioning strap that is wrapped around the thumb, through and around the splint, passed through the loop and secured on itself with the pressure sensitive adhesive, the mating strap adapted to pull the thumb inward against the hand, increase grip strength and protect the thumb.

7. An immobilizing thumb support according to claim 6, the glove further comprising a wrist area having a pressure sensitive adhesive; and, the strap system further comprising a wrist strap that is fixed to the wrist area of the glove and having a corresponding pressure sensitive adhesive, whereby the wrist strap can be wrapped to a comfortable fit and anchored on the wrist area to stabilize the glove.

8. An immobilizing thumb support according to claim 7, wherein the repositioning thumb splint further comprises a wider body portion positioned over and providing protection of a thumb metacarpal; a head portion that is smaller than the body, the head portion interconnected to the body by the narrowed integral flex portion, forming a neck piece and the head having a projecting thumb tab, whereby the head can flex on the body and the tab can flexibly surround and protect a first thumb phalanx while the splint is controlled and biased against a hand for continued function of an injured thumb within the splint to enhance grip strength.

9. An apparatus to prevent hyperextension of a thumb, comprising:

a glove having a wrist strap to retain the glove, a tensioning strap and all straps having a pressure sensitive adhesive, and a tension loop to receive the tensioning strap for interconnecting the splint and the glove with an appropriate tension to control function of the splint concomitant with a grip of the hand;

a rigid repositionable splint mounted on a thumb, said splint having an attached sizing strap to fit the splint on a thumb and an attached positioning strap to retain the splint in a comfortable position on a hand.

10. An apparatus as described in claim 9, wherein the splint is preshaped for conformity to an individual thumb, whereby the apparatus is preformed for preventing hyperextension of a thumb.

11. An apparatus as described in claim 10, wherein the preshaped splint having a wider body portion comprises a rigid covering for functional support at a metacarpophalangeal articulation and protection of a thumb.

12. An apparatus as described in claim 11, the glove further comprising a thumb section with a thumb base to receive a thumb therein; and, wherein the splint is mounted on the thumb section.

13. An apparatus according to claim 12, further comprising a means for sizing the splint for adjustment of the splint on a thumb, said means for sizing wrapped on a second phalange of the thumb.

14. An apparatus according to claim 13, wherein the means for sizing comprises the splint having a flexible projecting thumb tab with an application of a pressure sensitive adhesive; and the sizing strap having two ends, the first end fixed to the splint and the second end having a pressure sensitive adhesive, whereby the sizing strap can be wrapped over the splint thumb tab and detachably anchored on the splint tab to partially girdle a thumb.

15. An apparatus according to claim 14, further comprising a means for situating the splint on a thumb, the means for situating rotatably fixed to the splint.

16. An apparatus according to claim 15, wherein the means for situating comprises the splint wider body portion including a broad base section with anterior and posterior sides, the anterior splint side having a pressure sensitive adhesive; a strap retainer fixed to the splint base section near the posterior side; and the positioning strap having first and second ends for comfortably situating the splint on a thumb phalanx, the first position strap end rotatably mounted on the strap retainer of the splint, and the second position strap end having a pressure sensitive adhesive, whereby the position strap is adapted to encircle the wrist, detachably anchor on the splint anterior side and situate the splint as desired for comfort.

17. An apparatus according to claim 16, the tensioning strap further comprising a repositioning strap portion with first and second ends and a middle, the first end sewn to the glove posterior near the thumb base; the repositioning strap portion second end and middle having a pressure sensitive adhesive;

the tension loop further comprising a mating strap with first and second ends, the first end sewn to the glove anterior and the second end having a buckle to receive the repositioning strap portion with its first end and middle detachably interconnected by the pressure sensitive adhesive, for repositioning the thumb splint toward the hand when gripping an object.

18. A method for using a protective apparatus to prevent injury to a thumb, the apparatus comprising a specialized glove and a rigid thumb splint having a sizing strap to fit the splint on a thumb and a positioning strap to retain the splint in a comfortable position on a hand, the glove having a wrist strap to retain the glove, a tensioning strap and all straps having a pressure sensitive adhesive, and a tension loop to receive the tensioning strap for interconnecting the splint and the glove with an appropriate tension to control function of the splint concomitant with a grip of the hand, comprising the steps of:

molding a thumb splint for conformity to an individual thumb;

placing the specialized glove on a hand;

wrapping the wrist strap around a wrist;

mounting the premolded thumb splint over a thumb;

wrapping the sizing strap around the splint over a thumb;

wrapping the positioning strap around a hand;

wrapping the tensioning strap around the thumb, through and around the splint, and through the tension loop;

anchoring all straps with pressure sensitive adhesives.

19. A thumb support for use by a person having an injured thumb for enabling continued participation in sporting activities with diminished risk of reinjury, but without diminishing grip strength, the thumb support comprising:

a glove worn by a person having an injured thumb;

means for stabilizing an injured thumb, comprising a repositioning thumb splint, constructed of a thermally moldable material for thermal shaping of the splint to an injured thumb, mounted over the glove to immobilize and fortify an injured thumb while maintaining grip strength provided by a thumb;

means for biasing that articulates with the glove and the stabilizing means for control of an injured thumb and the stabilizing means;

wherein the repositioning thumb splint is a preformed rigid piece fitted over the glove;

the means for biasing comprising a splint strap system for retaining the splint in a preferred position on an injured thumb;

a glove strap system for providing a tension for increased grip strength of an injured thumb, comprising a splint sizing strap having first and second ends with the first end fixed to the splint and the second end having a pressure sensitive adhesive to retain the splint in a preadjusted position and to secure the sizing strap second end that is wrapped around the splint; and, further comprising a splint positioning strap having first and second ends, a strap retainer fixed to the splint for attachment of the positioning strap first end to the splint, the second positioning strap end having a pressure sensitive adhesive to secure the positioning strap second end that is wrapped around a person's wrist to the splint.

20. An immobilizing thumb support according to claim 19, the glove strap system further comprising a tensioning strap having first and second ends and a mid-section, the tensioning strap first end fixed to the glove near a thumb base, the second tensioning strap end and mid-section having pressure sensitive adhesive;

a mating strap having first and second ends, the mating strap first end fixed to the glove near a base of a little finger and a tension loop secured to the second end of the mating strap to receive the tensioning strap that is wrapped around the thumb, through and around the splint, passed through the loop and secured on itself with the pressure sensitive adhesive, the mating strap adapted to pull the thumb inward against the hand, increase grip strength and protect the thumb.

21. An immobilizing thumb support according to claim 20, the glove further comprising a wrist area having a pressure sensitive adhesive; and, the strap system further comprising a wrist strap that is fixed to the wrist area of the glove and having a corresponding pressure sensitive adhesive, whereby the wrist strap can be wrapped to a comfortable fit and anchored on the wrist area to stabilize the glove.

22. An immobilizing thumb support according to claim 21, wherein the repositioning thumb splint further comprises a wider body portion for positioning over and protection of a thumb metacarpal; a head portion that is smaller than the body, the head portion interconnected to the body by a narrow neck piece and the head having a projecting thumb tab, whereby the head can flex on the body and the tab can flexibly surround and protect a first thumb phalanx while the splint is controlled and biased against a hand for continued function of an injured thumb within the splint to enhance grip strength.

23. An apparatus to prevent hyperextension of a thumb, comprising:

a glove with a repositionable splint mounted on a thumb, and means for repositioning the splint associated with the glove; wherein said splint is preshaped for correspondence to an individual thumb, whereby the apparatus is preformed for preventing hyperextension of a thumb wherein the preshaped splint comprises a rigid covering for protection of a thumb;

the glove further comprising a thumb section with a thumb base to receive a thumb therein; and, wherein the splint is mounted on the thumb section;

further comprising a means for sizing the splint for adjustment of the splint on a thumb, comprising the splint having a flexible thumb tab with an application of a pressure sensitive adhesive; and a sizing strap having two ends, the first end fixed to the splint and the second end having a pressure sensitive adhesive, whereby the sizing strap can be wrapped over the splint thumb tab and detachably anchored on the splint tab to partially girdle a thumb;

further comprising a means for situating the splint on a thumb, the means for situating rotatably fixed to the splint, comprising the splint having a broad base section with anterior and posterior sides, the anterior splint side having a pressure sensitive adhesive; a strap retainer fixed to the splint base section near the posterior side; and a position strap with first and second ends for comfortably situating the splint on a thumb phalanx, the first position strap end rotatably mounted on the strap retainer of the splint, and the second position strap end having a pressure sensitive adhesive, whereby the position strap is adapted to encircle the wrist, detachably anchor on the splint anterior side and situate the splint as desired for comfort.

24. An apparatus according to claim 23, the means for repositioning comprising the glove having an anterior and posterior and first and second strap assemblies; the first assembly comprising a repositioning strap portion with first and second ends and a middle, the first end sewn to the glove posterior near the thumb base; the repositioning strap second end and middle having a pressure sensitive adhesive;

the second strap assembly comprising a mating strap with first and second ends, the first end sewn to the glove anterior and the second end having a buckle to receive the repositioning strap portion with its first end and middle detachably interconnected by the pressure sensitive adhesive, for repositioning the thumb splint toward the hand when gripping an object.

* * * * *